W. HALL.

Lightning Rod.

No. 2,888. Reissued March 3, 1868.

Attest:
J. M. Kenney
W. A. M. Kenney

Inventor:
William Hall.

N. PETERS, Photo-Lithographer, Washington, D. C.

UNITED STATES PATENT OFFICE.

WILLIAM HALL, OF DUBUQUE, IOWA.

IMPROVEMENT IN LIGHTNING-RODS.

Specification forming part of Letters Patent No. 25,823, dated October 18, 1859; Reissue No. 2,888, dated March 3, 1868.

*To all whom it may concern:*

Be it known that I, WILLIAM HALL, of the city of Dubuque, in the county of Dubuque and State of Iowa, have invented a new and useful Improvement in Lightning-Rods; and I do hereby declare that the following is a full and exact description of the manner of constructing the same, reference being had to the annexed drawings, in which—

Figure 1:
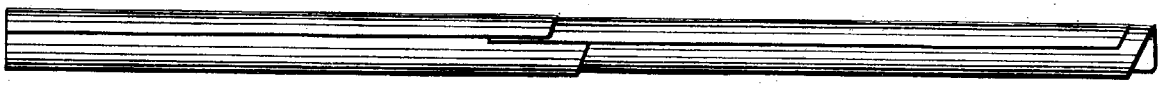
Figure 2:
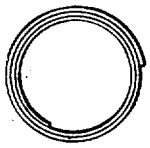

Figure 1 represents two sections of the rod, and Fig. 2 an end view of the same.

I cut a strip of copper plate any width desired and of a convenient length, ordinarily about sixty inches. Then, by means of an iron or steel rod having a slot or groove in one side, I roll this sheet up into a scroll, letting it extend once around, or more than once, in order to give as great capacity as I desire. These sections are put together in such a manner that the entire surfaces of consecutive sections may come in contact, and secure them together by any convenient and safe method. The edges of the scroll are left open, in order that the electric currents may have unobstructed circulation over both the inside and the outside surfaces.

What I claim as my invention, and desire to secure by Letters Patent as an article of manufacture, is—

A cylindrical lightning-rod made of sheet-copper, in sections, where the sheet is made to extend beyond a single cylinder, leaving the edges open or unsoldered, when the same is constructed substantially as and for the purposes herein set forth.

WILLIAM HALL.

Witnesses:
J. MCKENNEY,
W. A. MCKENNEY.